(12) United States Patent
Magari et al.

(10) Patent No.: US 7,361,510 B2
(45) Date of Patent: Apr. 22, 2008

(54) METHODS OF DETECTION OF IRON DEFICIENCY

(75) Inventors: Robert T. Magari, Cooper City, FL (US); Ramon Simon-Lopez, St. Cergue (CH)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/624,855

(22) Filed: Jan. 19, 2007

(65) Prior Publication Data

US 2007/0172956 A1 Jul. 26, 2007

Related U.S. Application Data

(60) Provisional application No. 60/760,520, filed on Jan. 20, 2006.

(51) Int. Cl.
*G01N 33/48* (2006.01)
*G01N 33/72* (2006.01)

(52) U.S. Cl. ............... 436/63; 436/10; 436/66; 436/84; 435/2

(58) Field of Classification Search ............ 436/8, 436/10, 63, 66, 84; 435/2; 530/385
See application file for complete search history.

(56) References Cited

U.S. PATENT DOCUMENTS

| | | | |
|---|---|---|---|
| 2,656,508 A | 10/1953 | Coulter | |
| 3,810,011 A | 5/1974 | Coulter et al. | |
| 4,030,888 A * | 6/1977 | Yamamoto et al. | 422/67 |
| 4,521,518 A | 6/1985 | Carter et al. | |
| 4,528,274 A | 7/1985 | Carter et al. | |
| 5,125,737 A | 6/1992 | Rodriguez et al. | |
| 5,686,309 A | 11/1997 | Frank et al. | |
| 5,763,280 A | 6/1998 | Li et al. | |
| 5,834,315 A | 11/1998 | Riesgo et al. | |
| 5,851,835 A | 12/1998 | Groner | |
| 5,882,934 A | 3/1999 | Li et al. | |
| 5,935,857 A | 8/1999 | Riesgo et al. | |
| 6,030,838 A * | 2/2000 | Telmissani | 436/63 |
| 6,228,652 B1 * | 5/2001 | Rodriguez et al. | 436/63 |
| 6,268,217 B1 * | 7/2001 | Barton et al. | 436/66 |
| 6,573,102 B2 | 6/2003 | Li et al. | |
| 6,706,526 B2 | 3/2004 | Lang et al. | |
| 6,916,662 B2 * | 7/2005 | Kendall et al. | 436/70 |
| 2003/0232393 A1 | 12/2003 | Roddiger et al. | |
| 2007/0072170 A1 * | 3/2007 | Simon-Lopez | 435/4 |
| 2007/0072300 A1 * | 3/2007 | Simon-Lopez | 436/43 |
| 2007/0172955 A1 * | 7/2007 | Qian et al. | 436/66 |

FOREIGN PATENT DOCUMENTS

JP 11-326315 * 11/1999

OTHER PUBLICATIONS

Bain, B.J., Blood Cells, A Practical Guide, Second Edition, Blackwell Science Ltd., 1995, Chapter 8, pp. 197-199.
Eknoyan, G., et al, "Continuous quality improvement: DOQI becomes K/DOQI and is updated". Am J Kidney Dis., Jan. 2001; 37(1): 179-194.
Eschbach, J., "Anemia Management in Chronic Kidney Disease: Role of Factors Affecting Epoetin Responsiveness". J. Am. Soc Nephrol 13: 1412-1414, 2002.
Thomas, et al, "Biochemical Markers and Hematologic Indices in the Diagnosis of Functional Iron Deficiency", Clin Chem 48:7, 1066-1076, 2002.
Machin, S.J., et al, "Functional Iron Deficiency and New Red Cell Parameters on the Sysmex XE-2100", ISLH XIVth Int'l Symposium, 2001.
Thomas, C., et al, "Anemia of Chronic Disease: Pathophysiology and Laboratory Diagnosis", Lab Hematology, vol. 11, pp. 14-23, 2005.
Locatelli, et al, "Revised European Best Practice Guidelines for the Management of Anaemia in Patients with Chronic Renal Failure", Nephrology and Dialysis Transplantation, vol. 19 Supp 2, May 2004, pp. ii22-ii24 and ii39-ii41.

* cited by examiner

*Primary Examiner*—Maureen M. Wallenhorst
(74) *Attorney, Agent, or Firm*—Cuspa Technology Law Associates; Mitchell E. Alter

(57) ABSTRACT

New diagnostic indexes and the method of use for detection of iron deficiency have been disclosed. These include a logistic function of mean cell hemoglobin (MCH) and mean cell volume (MCV), and a logistic function of mean cell hemoglobin concentration (MCHC) and MCH.

14 Claims, 1 Drawing Sheet

METHODS OF DETECTION OF IRON DEFICIENCY

CROSS REFERENCE TO RELATED APPLICATION

This application claims the benefit under 35 USC 119(e) of the provisional patent application Ser. No. 60/760,520, filed on Jan. 20, 2006, which is hereby incorporated by reference in its entirety.

FIELD OF THE INVENTION

The present invention relates to methods of detection of iron deficiency using functions of hematology parameters.

BACKGROUND OF THE INVENTION

Iron deficiency (ID) is the most prevalent single deficiency state on a worldwide basis. It is important economically because it diminishes the capability of individuals who are affected to perform physical labor, and it diminishes both growth and learning in children.

Absolute iron deficiency, with anemia or without anemia, and functional iron deficiency (FID) are high frequency clinical conditions, and these patients have iron deficient erythropoiesis. Absolute iron deficiency is defined as a decreased total iron body content. Iron deficiency anemia (IDA) occurs when iron deficiency is sufficiently severe to diminish erythropoiesis and cause the development of anemia. Functional iron deficiency describes a state where the total iron content of the body is normal or even elevated, but the iron is 'locked away' and unavailable for the production of red blood cells. This condition is observed mainly in patients with chronic renal failure who are on hemodialysis, and in patients with chronic inflammation or chronic infections.

Iron status can be measured using hematological and biochemical indices. Each parameter of iron status reflects changes in different body iron compartments and is affected at different levels of iron depletion. Specific iron measurements include hemoglobin (Hgb), mean cell volume (MCV), hematocrit (Hct), erythrocyte protoporphyrin, plasma iron, transferrin, transferrin saturation levels (TSAT), serum ferritin (SF) and more recently soluble transferrin receptors (sTfR) and red-cell distribution width (RDW).

Typical values for normal iron status are SF 100±60 ng/ml and Hgb 12-17 g/dl for women and 14-19 g/dl for men. The typical values for iron deficiency anemia are SF <22 ng/ml, Hgb for women <12 g/dl and for men <13 g/dl.

Hemoglobin (Hgb) has been used longer than any other iron status parameter. It provides a quantitative measure of the severity of iron deficiency once anemia has developed. Hemoglobin determination is a convenient and simple screening method and is especially useful when the prevalence of iron deficiency is high, as in pregnancy or infancy. The limitations of using hemoglobin as a measure of iron status are its lack of specificity (as factors such as vitamin $B_{12}$ or folate deficiency, genetic disorders and chronic infections can limit erythropoiesis) and its relative insensitivity due to the marked overlap in values between normal and iron deficient populations. To identify iron deficiency anemia, hemoglobin is measured together with more selective measurements of iron status.

A reduction in mean cell volume (MCV) occurs when iron deficiency becomes severe, at about the same time as anemia starts to develop. It is a fairly specific indicator of iron deficiency once thalassemia and the anemia of chronic disease have been excluded. A cut-off value of 80 fl is accepted as the lower limit of normal in adults. It has been reported that when measured on Technicon hematology analyzers (that use optical measurement of red blood cells) iron deficiency blood samples have reduced mean cell hemoglobin (MCH), and mean cell hemoglobin concentration (MCHC). However, when measured by impedance-based hematology analyzers (Such as Coulter or Sysmex instruments) MCHC is insensitive but more specific for iron deficiency (Bain, B. J., Blood Cells, A Practical Guide, Second Edition, Blackwell Science Ltd., 1995, Chapter 8, pages 197-199). The red-cell distribution width (RDW) has been used recently in combination with other parameters for the classification of anemias. It reflects the variation in the size of the red cells and can be used to detect subtle degrees of anisocytosis.

The most commonly used iron status parameters at present are transferrin saturation (TSAT) and serum ferritin (SF). However, both are indirect measures of iron status. Transferrin is a transport protein that contains two iron binding sites by which it transports iron from storage sites to erythroid precursors. TSAT (i.e., the percentage of total binding sites that are occupied by iron) is a measure of iron that is available for erythropoiesis. TSAT is calculated by dividing the serum iron by the total iron binding capacity (TIBC), a measurement of circulating transferrin, and multiplying by 100. Ferritin is a storage protein that is contained primarily within the reticuloendothelial system, with some amounts released in the serum. Under conditions of iron excess, ferritin production increases to offset the increase in plasma iron. The level of ferritin in the serum, therefore, reflects the amount of iron in storage.

| Definition of Functional Iron Deficiency (FID) and Absolute Iron Deficiency (AID) by Kidney Disease Outcomes, Quality Initiative K/DOQI (U.S.A) | | |
|---|---|---|
| Ferritin µg/L | <100 | 100–800 |
| TSAT <20% | AID | |
| TSAT <20% | | FID |

For patients with chronic kidney disease, absolute iron deficiency may be diagnosed when TSAT is <20% and SF is <100 ng/ml. Functional iron deficiency may be more difficult to diagnose since iron status parameters may indicate adequate iron stores. There are different criteria in defining FID, one of them is published by the Kidney Disease Outcomes Quality Initiative—K/DOQI (Eknoyan G, et al. Continuous quality improvement: DOQI becomes K/DOQI and is updated. National Kidney Foundation's Dialysis Outcomes Quality Initiative. *Am J Kidney Dis.*, 2001 January; 37(1):179-194; Anemia Management in Chronic Kidney Disease: Role of Factors Affecting Epoetin Responsiveness, ESCHBACH, J., *J Am Soc Nephrol* 13: 1412-1414, 2002.), as shown in the table above.

The limitations of using transferrin saturation reflect those of serum iron, i.e., wide diurnal variation and low specificity. TSAT is also reduced in inflammatory disease. Transferrin saturation is commonly used in population studies combined with other indicators of iron status. On the other hand, as ferritin is an acute phase reactant, its serum levels may be elevated in the presence of chronic inflammation, infection, malignancy and liver disease. Alcohol consumption has also been suggested to independently raise serum ferritin.

Recently, several new red blood cell and reticulocyte parameters have been reported having utilities in detection of iron deficiency and functional iron deficiency. Two of the parameters are hypochromic red cell percentage (referred to as % Hypo) and CHr (reticulocyte hemoglobin content) reported by the Bayer ADVIA 120 hematology analyzer (Thomas et al., Biochemical Markers and Hematologic Indices in the Diagnosis of Functional Iron Deficiency, *Clinical Chemistry* 48:7, 1066-1076, 2002). Hypochromic red cell percentage is defined as the percentage of red blood cells having hemoglobin less than 28 g/dl. CHr is defined by the formula (CHr=MCVr×CHCMr), wherein MCVr is the mean reticulocyte cell volume and CHCMr is the mean hemoglobin concentration of reticulocytes which is obtained by an optical cell-by-cell hemoglobin measurement.

Reticulocytes are immature red blood cells with a life span of only 1 to 2 days. When these are first released from the bone marrow, measurement of their hemoglobin content can provide the amount of iron immediately available for erythropoiesis. A less than normal hemoglobin content in these reticulocytes is an indication of inadequate iron supply relative to demand. The amount of hemoglobin in these reticulocytes also corresponds to the amount of hemoglobin in mature red blood cells. CHr has been evaluated recently in numerous studies as a test for iron deficiency and functional iron deficiency and has been found to be highly sensitive and specific. However, exact threshold values have not been established, as the threshold values vary depending on the laboratory and instrument used.

Epoetin is effective in stimulating production of red blood cells, but without an adequate iron supply to bind to heme, the red blood cells will be hypochromic, i.e., low in hemoglobin content. Thus, in states of iron deficiency, a significant percentage of red blood cells leaving the bone marrow will have a low hemoglobin content. By measuring the percentage of red blood cells with hemoglobin content <28 g/dl, iron deficiency can be detected. % Hypo >10% has been correlated with iron deficiency, and hence has been used as a diagnostic criterion for detection of iron deficiency (Revised European Best Practice Guidelines for the Management of Anaemia in Patients With Chronic Renal Failure, Locatelli, F. et al., *Nephrology and Dyalisis Transplantation*, Volume 19 May 2004 (Supplement 2), Guideline III.2, page ii22-24).

% Hypo is a reported parameter on several Bayer hematology analyzers based on an optical cell-by-cell hemoglobin measurement. % Hypo must be measured using a fresh whole blood sample (less than four hours after blood collection), since storage or sample aging leads to erroneous increases of % Hypo report due to red blood cell swelling (Revised European Best Practice Guidelines for the Management of Anaemia in Patients With Chronic Renal Failure, Locatelli, F. et al., *Nephrology and Dyalisis Transplantation*, Volume 19 May 2004 (Supplement 2), Appendix B, page ii39-41).

Two other parameters have been reported recently correlating to % Hypo and CHr are RBC-Y and Ret-$H_e$ reported by the Sysmex XE-2100 hematology analyzer (Machin S. J. et al. Functional Iron Deficiency and New Red Cell Parameters on the Sysmex XE-2100, ISLH 2001 Industry-Sponsored Workshops, ISLH XIVth International Symposium, 2001; and Thomas, C. et al., Anemia of Chronic Disease: Pathophysiology and Laboratory Diagnosis, *Laboratory Hematology* 2005, 11:14-23). RBC-Y is the mean value of the forward light scatter histogram within the mature erythrocyte population, and Ret-$H_e$ is the mean value of the forward light scatter histogram within the reticulocyte population obtained in a reticulocyte measurement on the Sysmex XE-2100 hematology analyzer.

Most recently, several functions of red blood cell parameters as well as reticulocyte parameters have been disclosed by Simon-Lopez in the co-pending application Ser. No. 11/524,682 to be useful in detection of iron deficiency. These include a RBC size function (RSf) defined as a product function of MCV and MRV, a volume-hemoglobin factor (VHf) defined as a product function of MCV and Hgb, a volume-hemoglobin/distribution factor (VHDWf) defined as a function of MCV, Hgb and RDW.

It has been recognized that CHr and % Hypo are only provided on Bayer's hematology analyzers. Therefore, this information is not available for many clinical laboratories and hospitals. On the other hand, MCV, MCH, MCHC and Hgb are the traditional red cell indices provided on all automated hematology analyzers. Because of the availability of these traditional red blood cell parameters, it is desirable to develop diagnostic indicators using these parameters for detection iron deficiency with comparable clinical accuracy, sensitivity and specificity to the known parameters such as CHr and % Hypo.

SUMMARY OF THE INVENTION

In one aspect, the present invention provides methods of detection of iron deficiency.

In one embodiment, the present invention is directed to a method of detection of iron deficiency using a new iron deficiency index ($IDI_1$) that has a similar diagnostic ability as CHr in detection of iron deficiency. The method comprises the steps of analyzing a blood sample on a hematology analyzer and obtaining mean cell hemoglobin (MCH) and mean cell volume (MCV) of red blood cells; obtaining an iron deficiency index ($IDI_1$) defined as a function of the MCH and the MCV; comparing the $IDI_1$ to a predetermined $IDI_1$ iron deficiency criterion; and reporting an indication of iron deficiency if the $IDI_1$ meets the predetermined $IDI_1$ iron deficiency criterion.

In one embodiment, $IDI_1$ is a logistic function of MCH and MCV defined by the equation of $IDI_1=\exp(a+b*MCV+c*MCH)/(1+\exp(a+b*MCV+c*MCH))$, wherein a, b and c are constants. In one exemplary embodiment, a, b and c are −35.6, 0.087 and 1.61, respectively, and the predetermined $IDI_1$ iron deficiency criterion defines iron deficiency if the $IDI_1$ is equal to or less than 0.9.

In a further embodiment, the present invention is directed to a method detection of iron deficiency using an iron deficiency index ($IDI_2$) which has a similar diagnostic ability as % Hypo in detection of iron deficiency. The method comprises the steps of analyzing a blood sample on a hematology analyzer and obtaining mean cell hemoglobin concentration (MCHC) and mean cell hemoglobin (MCH) of red blood cells; obtaining an iron deficiency index ($IDI_2$) defined as a function of the MCHC and the MCH; comparing the $IDI_2$ to a predetermined $IDI_2$ iron deficiency criterion; and reporting an indication of iron deficiency if the $IDI_2$ meets the predetermined $IDI_2$ iron deficiency criterion.

In one embodiment, $IDI_2$ is a logistic function of MCH and MCHC defined by the equation of $IDI_2=\exp(i+j*MCH+k*MCHC)/(1+\exp(i+j*MCH+k*MCHC))$, wherein i, j and k are constants. In one exemplary embodiment, i, j and k are −97.98, 0.24 and 2.91, respectively, and the predetermined $IDI_2$ iron deficiency criterion defines iron deficiency if the $IDI_2$ is equal to or less than 0.59.

In a further aspect, the present invention provides methods of producing the above defined iron deficiency indexes on hematology analyzers.

In one embodiment, the method of producing iron deficiency index ($IDI_1$) of a blood sample on a hematology analyzer comprises the steps of mixing a first aliquot of a blood sample with a blood diluent to form a first sample mixture, analyzing the first sample mixture on the hematology analyzer, and obtaining a mean cell volume of red blood cells (MCV) and a red blood cell concentration (RBC); mixing a second aliquot of the blood sample with a reagent system to form a second sample mixture, analyzing the second sample mixture on the hematology analyzer, and obtaining a hemoglobin concentration (Hgb) of the blood sample; obtaining mean cell hemoglobin (MCH) using the obtained RBC and Hgb; obtaining the iron deficiency index ($IDI_1$) using the obtained MCV and MCH; and reporting $IDI_1$ of the blood sample on the hematology analyzer.

In a further embodiment, the method of producing the iron deficiency index ($IDI_2$) of a blood sample on a hematology analyzer comprises mixing a first aliquot of a blood sample with a blood diluent to form a first sample mixture, analyzing the first sample mixture on the hematology analyzer, and obtaining a mean cell volume of red blood cells (MCV) and a red blood cell concentration (RBC); mixing a second aliquot of the blood sample with a reagent system to form a second sample mixture, analyzing the second sample mixture on the hematology analyzer, and obtaining a hemoglobin concentration (Hgb) of the blood sample; obtaining mean cell hemoglobin (MCH) and mean cell hemoglobin concentration (MCHC) using the obtained MCV, RBC and Hgb; obtaining the iron deficiency index ($IDI_2$) using the obtained MCH and MCHC; and reporting $IDI_2$ of the blood sample on the hematology analyzer.

The advantages of the present invention will become apparent from the following description taken in conjunction with the accompanying drawings showing exemplary embodiments of the invention.

DETAILED DESCRIPTION OF THE INVENTION

Figure 1:
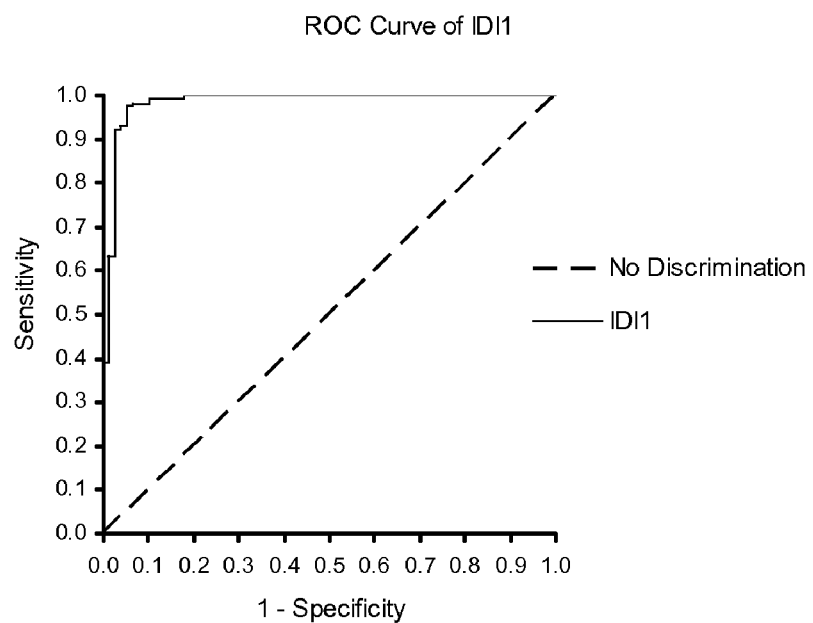
FIG. 1 is the ROC curve of $IDI_1$, as described in Example 1.

In one embodiment, the present invention provides a method for detection of iron deficiency using an iron deficiency index ($IDI_1$) defined as a function of mean cell hemoglobin (MCH) and mean cell volume (MCV). The term of iron deficiency used herein includes absolute iron deficiency, and functional iron deficiency (FID).

Absolute iron deficiency, frequently referred to as iron deficiency in the literature, is defined as a decreased total iron body content. Iron deficiency anemia (IDA) occurs when iron deficiency is sufficiently severe to diminish erythropoiesis and cause the development of anemia. Latent iron deficiency refers to the presence of iron deficiency but not yet anemia. On the other hand, functional iron deficiency defines a state where the total iron content of the body is normal or even elevated, but the iron is unavailable for the production of red blood cells. This condition is observed mainly in patients with chronic renal failure who are on hemodialysis. Latent functional iron deficiency refers to the pre-anemic stage of functional Iron deficiency. Individuals having different forms of iron deficiency, as described above, have different extents of iron deficient erythropoiesis.

More specifically, the method comprises the following steps: (a) analyzing a blood sample on a hematology analyzer and obtaining MCH and MCV of the blood sample; (b) obtaining an iron deficiency index ($IDI_1$) defined as a function of MCH and MCV; (c) comparing the $IDI_1$ to a predetermined $IDI_1$ iron deficiency criterion; and (d) reporting an indication of iron deficiency if the $IDI_1$ meets the predetermined $IDI_1$ iron deficiency criterion.

The iron deficiency index ($IDI_1$) is a logistic function of MCH and MCV defined by the following equation:

$$IDI_1 = \exp(a + b*MCV + c*MCH)/(1 + \exp(a + b*MCV + c*MCH))$$

wherein a, b and c are constants. In one embodiment, a, b and c are −35.6, −0.087 and 1.61, respectively. Moreover, in an exemplary embodiment the predetermined $IDI_1$ iron deficiency criterion defines iron deficiency if $IDI_1$ is equal to or less than 0.9. It is noted that a specific iron deficiency criterion, such as the $IDI_1$ iron deficiency criterion described herein, is also commonly referred to as the cut-off value for diagnosis of the clinical condition, as used in the examples described hereinafter.

The mean cell hemoglobin (MCH), also referred to as hemoglobin amount per red blood cell, is defined as MCH=Hgb/RBC*10, wherein Hgb is the total hemoglobin concentration of a blood sample, and RBC is the red blood cell concentration in the blood sample, which is commonly referred to as red blood cell count. On an automated hematology analyzer, Hgb and RBC are typically measured separately using two aliquots of a blood sample, as described in detail hereinafter, and MCH is derived from the obtained Hgb and RBC. However, MCH can also be measured by an optical cell-by-cell hemoglobin measurement of individual red blood cells, without lysing the blood sample. For the purpose of the present invention, MCH can be obtained using either approach.

In the measurement of red blood cells on a hematology analyzer a blood sample is typically diluted substantially with a diluent in a sample chamber or bath. Using an impedance measurement with a non-focused flow aperture, the blood sample can be highly diluted, for example with a dilution ratio of 6250:1. When a non-focused flow cell is used for the measurement, the dilution ratio can be substantially lower, such as 290:1. To maintain the volume and morphology of the red blood cells during their measurements on a hematology analyzer, an isotonic diluent is used for diluting the blood sample. Typically, the diluent contains one or more alkaline metal salts. Various commercially available isotonic blood diluents can be used for diluting the blood sample. Suitable examples include, but are not limited to, the diluents described in U.S. Pat. Nos. 4,521,518, 4,528,274, 5,935,857 and 6,706,526.

When a particle or a blood cell, suspended in a conductive aqueous solution, passes through a flow cell or an aperture, an electrical signal, or a pulse, can be measured due to the increase of impedance. The electrical pulses have been used for counting the number of blood cells of a blood sample. On the other hand, the pulse shape, height and width are directly related to the volume or size of a particle, and can be converted to the volume of the cell measured. When a sample that contains two or more different blood cells having different volumes is measured, a histogram obtained from the measurement can represent volume distribution of these blood cells. The detection methods and apparatus used for blood cell counting and sizing by a blood analyzer equipped with a DC impedance measurement device are generally described in U.S. Pat. Nos. 2,656,508, 3,810,011 and 5,125,737, which are hereby incorporated by reference in their entirety. Herein, the phrase "blood cell sizing" refers to the cell volume measurement.

Alternatively, low angle light scatter measurement can also be used for counting and sizing the blood cells. Herein, the term "low angle light scatter" refers to the light scatter signals measured in a range in less than 10° from the incident light.

In the cell volume measurement a cell volume distribution histogram is obtained. For the red blood cell measurement, the obtained histogram is referred to as the red blood cell distribution histogram. For a normal blood sample, a narrow and well defined red blood cell distribution, typically a Gaussian distribution, is obtained. For clinically abnormal blood samples, various distortions of the distribution have been observed, such as shift of the distribution to either higher or lower volume side, asymmetric distribution, population extension on either the higher or lower volume side, or both sides. The mean cell volume (MCV) and red blood cell distribution width (RDW) are calculated from the red blood cell distribution histogram.

The total hemoglobin concentration (Hgb) of a blood sample is typically measured on an automated hematology analyzer by mixing an aliquot of a blood sample with a lytic reagent. Upon exposing to the lytic reagent, the red blood cells are completely lysed, and hemoglobin is released to the sample mixture, which upon reacting with a ligand in the lytic reagent forms a chromogen. The hemoglobin chromogen is then measured by UV-VIS spectroscopy at a predetermined wavelength, and Hgb is calculated from the measurement.

One lysing reagent system suitable for measuring Hgb comprises an isotonic blood diluent, such as the diluents described in U.S. Pat. Nos. 4,521,518, 4,528,274, 5,935,857 and 6,706,526, and a lysing reagent, such as the lysing reagents described in U.S. Pat. Nos. 5,763,280, 5,834,315 and 6,573,102, these are hereby incorporated by reference in their entirety. Alternatively, the reagent system can also be a single lysing reagent as described in U.S. Pat. No. 5,882,934 which is hereby incorporated by reference in its entirety. Furthermore, various lytic reagents known in the art for measurement of hemoglobin can be used for the purpose of the present invention.

On the Coulter LH750 or GEN*S hematology analyzer (Beckman Coulter, Inc. Fullerton, Calif.), several aliquots of a blood sample are analyzed concurrently in different analysis modes. In the CBC mode, a first aliquot of a blood sample is diluted by a diluent to form a first sample mixture, and red blood cells and platelets are measured from the first sample mixture. At the same time, a second aliquot of the blood sample is mixed with a diluent and a lytic reagent to form a second sample mixture, and the hemoglobin concentration is measured using the second sample mixture. Various red blood cell parameters, among others, are reported from these measurements, which include red blood cell concentration (RBC), mean cell volume (MCV), total hemoglobin concentration (Hgb), mean cell hemoglobin (MCH), mean cell hemoglobin concentration (MCHC), and etc. On these hematology analyzers, MCH and MCHC are derived parameters calculated from MCV, RBC and Hgb.

As discussed above, CHr (reticulocyte hemoglobin content) reported by the Bayer hematology analyzer has been used for detection of iron deficiency and functional iron deficiency in the recent years and has been found to be highly sensitive and specific. Typically, a cut-off value of CHr <28 pg or <29 pg is used for determining absolute iron deficiency and functional iron deficiency.

Example 1 illustrates the method of the present invention using the iron deficiency index ($IDI_1$) defined above for detection of absolute iron deficiency and functional iron deficiency in comparison to CHr. A receiver operating characteristic (ROC) analysis of $IDI_1$ was performed on 247 clinical whole blood samples using CHr $\leq$28 pg as the criterion for defining iron deficiency. FIG. 1 shows the ROC curve of $IDI_1$. On the y-axis is plotted sensitivity (true positive fraction) and on the x-axis is plotted specificity (false positive fraction). A test with perfect discrimination has an ROC curve that passes through the upper left corner, where the true-positive fraction is 100% (perfect sensitivity). The theoretical curve for a test with no discrimination is 45° diagonal line from the lower left corner to the upper right corner. The closer the curve to the upper left corner, the higher the overall accuracy of the test is. Furthermore, the area under the ROC curve (AUC) is also a common measure of the clinical accuracy of a diagnostic test.

Table 1 shows the statistic analysis results. As shown, AUC is 0.9841 for $IDI_1$, which indicates that $IDI_1$ correlates highly with CHr. The values of AUC and ROC curves have indicated that $IDI_1$ has similar diagnostic ability as CHr in detection of iron deficiency. With a cut-off equal to 0.5, $IDI_1$ has a sensitivity of 94.9% and a specificity of 97.6%. It is noted that mathematically, a cut-off value of 0.5 gives the highest sensitivity and specificity. However, clinically the sensitivity is more important for detection of a clinical condition. It is found that with a cut-off equal to 0.9, $IDI_1$ has a sensitivity of 97.4% and a specificity of 89.9%.

It is noted that the recommended cut-off for CHr can be different depending on the specific Bayer hematology analyzer used. In a comparative study, the setting of the comparator's criterion can affect the cut-off value, as well as constants a, b and c in the equation of $IDI_1$. For example, in Example 1 if CHr $\leq$29 pg is the criterion used for defining iron deficiency, the constants a, b and c in the equation of $IDI_1$ are −36.156, −0.199 and 1.96, respectively. With a cut-off equal to 0.585, $IDI_1$ has a sensitivity of 95.7% and a specificity of 95.2%. In this case, the predetermined $IDI_1$ iron deficiency criterion defines iron deficiency if $IDI_1$ is equal to or less than 0.585.

In a further embodiment, the present invention provides a method using a second iron deficiency index ($IDI_2$) defined as a function of MCHC and MCH for detection of iron deficiency. More specifically, the method comprises the following steps: (a) analyzing a blood sample on a hematology analyzer and obtaining MCHC and MCH of the blood sample; (b) obtaining an iron deficiency index ($IDI_2$) defined as a function of the MCHC and the MCH; (c) comparing $IDI_2$ to a predetermined $IDI_2$ iron deficiency criterion; and (d) reporting an indication of iron deficiency if the $IDI_2$ meets the predetermined $IDI_2$ iron deficiency criterion. It has been found that using the function of MCHC and MCH, the clinical accuracy for detection iron deficiency can be enhanced.

In one embodiment, the second iron deficiency index ($IDI_2$) is a logistic function of MCH and MCHC defined by the following equation:

$$IDI_2 = \exp(i + j*MCH + k*MCHC)/(1 + \exp(i + j*MCH + k*MCHC))$$

wherein i, j and k are constants. In one exemplary embodiment, i, j and k are −97.98, 0.24 and 2.91, respectively, and the predetermined $IDI_2$ iron deficiency criterion defines iron deficiency if $IDI_2$ is equal to or less than 0.59.

Mean cell hemoglobin concentration (MCHC), also referred to as hemoglobin concentration per red blood cell, is defined by the equation MCHC=(Hgb/(RBC*MCV)) *1000. The measurements of Hgb, RBC and MCV have been described above. On most automated hematology analyzers, MCHC is derived from these directly measured parameters. Furthermore, MCHC can be obtained by cell volume measurement and an optical cell-by-cell hemoglobin measurement of hemoglobin of individual red blood cells, without lysing the cells. For the purpose of the present invention, MCHC can be obtained using either approach.

As discussed above, hypochromic red cell percentage (% Hypo) has also been used for determining iron deficiency. % Hypo <5% is considered normal. Two different criteria, more specifically, % Hypo >5% and >10% have been used. % Hypo >10% has been more commonly used for defining absolute iron deficiency and functional iron deficiency (Revised European Best Practice Guidelines for the Management of Anaemia in Patients With Chronic Renal Failure, Locatelli, F. et al., *Nephrology and Dyalisis Transplantation*, Volume 19 May 2004 (Supplement 2), Appendix B, page ii39-41).

Figure 2:
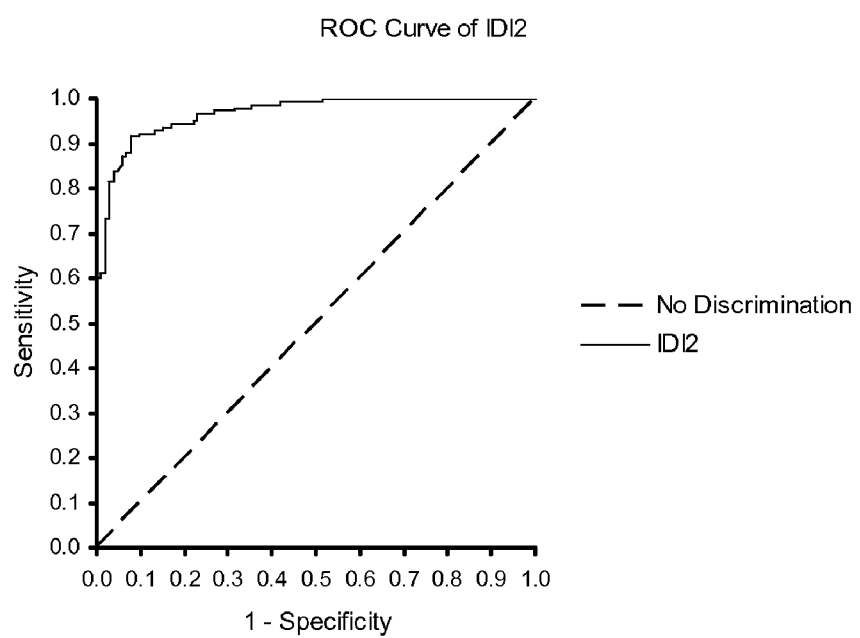
FIG. 2 is the ROC curve of $IDI_2$, as described in Example 2.

Example 2 illustrates the method of the present invention using iron deficiency index ($IDI_2$) defined above for detection of absolute iron deficiency and functional iron deficiency in comparison to % Hypo. A receiver operating characteristic (ROC) analysis of $IDI_2$ is performed on 247 clinical whole blood samples using % Hypo ≧10 as the criterion for defining iron deficiency. FIG. 2 shows the ROC curve of $IDI_2$.

The area under the ROC curve (AUC) for $IDI_2$ is 0.9675, illustrating that $IDI_2$ correlates highly with % Hypo. With a cut-off of 0.59, $IDI_2$ has a sensitivity of 92.4% and a specificity of 91.5%, respectively. The value of AUC and ROC curve have indicated that $IDI_2$ has a similar ability as % Hypo in detection of absolute iron deficiency and functional iron deficiency.

It is known that MCV, MCH or MCHC may reflect certain cellular characteristics under iron deficiency or iron deficient erythropoiesis condition. In iron deficient erythropoiesis, two abnormal cellular features are typically observed: hypochromia (low hemoglobin content in red blood cells), and microcytosis (low red blood cell volume). Historically, MCV, MCH or MCHC, individually has been used as indicators for iron deficiency in conjunction with other clinical chemistry or hematology parameters. The method of the present invention using $IDI_1$ or $IDI_2$ for detection of iron deficiency has advantages over the method of using one or more of these individual parameters.

First, $IDI_1$ is a logistic function of MCV and MCH, and $IDI_2$ is a logistic function of MCH and MCHC, respectively. Each index combines the effects of two different individual parameters, which can enhance the sensitivity, the specificity, or both, of the diagnostic index. Furthermore, both indexes are optimized to better distinguish between normal and iron deficiency samples, because logistic regression provides better discrimination between the two groups. Moreover, both indexes are scaled in the range of 0-1 (or 0-100%), which do not depend on the units of measurements of the individual parameters. As such, $IDI_1$ or $IDI_2$ can be used as an independent and effective index for detection of iron deficiency.

On the other hand, as described above, hypochromic red cell percentage must be measured using a fresh whole blood sample in less than 4 hours after blood collection, because sample aging leads to erroneous increases of % Hypo report due to red blood cell swelling. On the contrary, MCHC, MCH and MCV are stable at 24 hours after blood collection. As such, for the purpose of diagnosis of iron deficiency either $IDI_1$ or $IDI_2$ can be obtained using a routine hematology analysis of the whole blood sample, without being restricted by the narrow window of sample age as that required in the analysis of % Hypo. This provides a substantial advantage for the hematology laboratories in terms of sample handling and work flow management. For example, in various commercial hematology laboratories, many whole blood samples are collected in individual doctor's offices and sent to the laboratories for analysis. The blood samples are often received 24 hours or more after blood collection. These samples are no longer suitable for the analysis of % Hypo. However, reliable $IDI_1$ and $IDI_2$ can still be obtained with these 24 hour old samples.

It should be understood that the reported Hgb, MCV and RBC vary slightly among different hematology analyzers depending on the detection methods and the reagents used by different instrument manufacturers. Consequently, MCH and MCHC, the derived parameters, vary by a certain degree among different hematology analyzers. Therefore, the cut-off values, or the corresponding predetermined iron deficiency criteria for $IDI_1$ and $IDI_2$ in the method of the present invention can vary depending on the hematology analyzers used. Furthermore, it is known that Hgb, MCV and RBC, and the derived MCH and MCHC can vary depending on the patient demographics, as well as clinical focus of a particular hospital or facility, such as a cancer center or kidney dialysis center. As such, the cut-off values for $IDI_1$ and $IDI_2$ for the purpose of the present invention should be confirmed empirically for each hospital or the hematology analyzer used. The cut-off values for $IDI_1$ and $IDI_2$ obtained in the study shown herein exemplify the utility of the method of the present invention, and should not be construed as limitations of the present invention.

It can be appreciated MCHC, MCH and MCV are reported parameters on all commercial hematology analyzers produced by all manufacturers, including both high through-put instruments and the small instruments used in the doctor's office. Therefore, $IDI_1$ and $IDI_2$, the indexes required for detection of iron deficiency using the method of the present invention, can be obtained from all commercial hematology analyzers.

Furthermore, the method of the present invention using $IDI_1$ and $IDI_2$ for detections of iron deficiency is a time saving and low cost approach, because these parameters can be obtained from a routine hematology analysis of a whole blood sample without additional cost.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

247 clinical whole blood samples were analyzed on a Coulter LH750 and a Bayer ADVIA 120 hematology analyzer, respectively, at University College Hospital of London. All hematology analyzers were operated under their standard operating conditions, and calibrated using the calibration materials provided by the manufacturers according to the operator manual and the protocol of the study.

On the Coulter LH750 hematology analyzer (Beckman Coulter, Inc., Fullerton, Calif.), the sample was analyzed using the CBC and Retic modes. A first aliquot of 1.6 µl of a blood sample was diluted by Isoton 3E with a dilution ratio of 6250:1, to form a first sample mixture, which was measured by the DC impedance measurements to produce the red blood cell parameters. A second aliquot of 28 µl of the blood sample was diluted with 6 ml of Isoton 3E, and then mixed with 1 ml of Lyse S III diff to form a second sample mixture. The absorption of the second sample mixture was measured at about 540 nm to obtain Hgb. All reagents described above were the products of Beckman Coulter, Inc.

The iron deficiency index ($IDI_1$) was calculated using MCH and MCV reported from the Coulter LH750 hematology analyzer. $IDI_1$ was defined using the equation of $IDI_1 = \exp(-35.6 - 0.087*MCV + 1.61*MCH)/(1 + \exp(-35.6 - 0.087*MCV + 1.61*MCH))$. A receiver operating characteristic (ROC) analysis was performed on $IDI_1$ using CHr $\leq 28$ pg as the criterion for classifying normal and iron deficiency. More specifically, 78 blood samples having CHr $\leq 28$ pg were identified as iron deficiency or positive, and 169 samples having CHr >28 pg were identified as normal or negative. The obtained ROC curves are shown in FIG. 1 and the statistic data, including AUC, standard error (SE), p-value and 95% confidence interval, are shown in Table 1.

TABLE 1

Statistic Data of ROC Analysis of $IDI_1$ (CHr $\leq 28$ pg)

| Statistics | $IDI_1$ |
|---|---|
| AUC | 0.9841 |
| SE | 0.0092 |
| P-value | 0.0000 |
| Lower | 0.9660 |
| Upper | 1.0023 |

As shown, $IDI_1$ correlated highly with CHr. The value of AUC and ROC curve indicated that $IDI_1$ had similar diagnostic ability as CHr in detection of iron deficiency. The cut-off value for $IDI_2$ was obtained from the ROC analysis. With a cut-off equal to 0.5, $IDI_1$ had a sensitivity of 94.9% and specificity of 97.6%. To further increase sensitivity of $IDI_1$, a cut-off value of 0.9 was selected, which had sensitivity of 97.4% and specificity of 89.9%.

EXAMPLE 2

The hematology data of the same blood samples collected in Example 1 was for detection of iron deficiency using the iron deficiency index ($IDI_2$). $IDI_2$ was calculated using MCH and MCHC reported from the Coulter LH750 hematology analyzer. $IDI_2$ was defined using the equation of $IDI_2 = \exp(-97.98 + 0.24*MCH + 2.91*MCHC)/(1 + \exp(-97.98 + 0.24*MCH + 2.91*MCHC))$.

A ROC analysis was performed on $IDI_2$ using % Hypo >10% as the criterion for classifying normal and iron deficiency. More specifically, 105 blood samples having % Hypo >10% were identified as iron deficiency or positive, and 142 samples having % Hypo $\leq 10$% were identified as normal or negative. The obtained ROC curve is shown in FIG. 2 and the statistic data, including AUC, standard error (SE), p-value and 95% confidence interval, are shown in Table 2.

As shown, $IDI_2$ correlated excellently with % Hypo. The values of AUC and ROC curve indicated that $IDI_2$ had similar diagnostic abilities as % Hypo in detection of iron deficiency. The cut-off value for $IDI_2$ was obtained from the ROC analysis. With a cut-off of 0.59, $IDI_2$ had a sensitivity of 92.4% and a specificity of 91.5%, respectively.

TABLE 2

Statistic Data of ROC Analysis of $IDI_2$ (% Hypo >10%)

| Statistics | $IDI_2$ |
|---|---|
| AUC | 0.9675 |
| SE | 0.0701 |
| P-value | 0.0000 |
| Lower | 0.8301 |
| Upper | 1.1049 |

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of detection of iron deficiency comprising the steps of:
    (a) analyzing a blood sample on a hematology analyzer and obtaining mean cell hemoglobin (MCH) and mean cell volume (MCV) of red blood cells;
    (b) obtaining an iron deficiency index ($IDI_1$) defined as a logistic regression function of said MCH and said MCV;
    (c) comparing said $IDI_1$ to a predetermined $IDI_1$ iron deficiency criterion; and
    (d) reporting an indication of iron deficiency if said $IDI_1$ meets said predetermined $IDI_1$ iron deficiency criterion.

2. The method of claim 1, wherein said $IDI_1$ is defined by following equation:

$$IDI_1 + \exp(a + b*MCV + c*MCH)/(1 + \exp(a + b*MCV + c*MCH))$$

wherein a, b and c are constants.

3. The method of claim 2, wherein said a, b and c are −35.6, 0.087 and 1.61, respectively.

4. The method of claim 1, wherein said iron deficiency comprises absolute iron deficiency or functional iron deficiency.

5. A method of detection of iron deficiency comprising the steps of:
    (a) analyzing a blood sample on a hematology analyzer and obtaining mean cell hemoglobin concentration (MCHC) and mean cell hemoglobin (MCH) of red blood cells;
    (b) obtaining an iron deficiency index ($IDI_2$) defined as a logistic regression function of said MCHC and said MCH;
    (c) comparing said $IDI_2$ to a predetermined $IDI_2$ iron deficiency criterion; and
    (d) reporting an indication of iron deficiency if said $IDI_2$ meets said predetermined $IDI_2$ iron deficiency criterion.

6. The method of claim 5, wherein said $IDI_2$ is defined by following equation:

$$IDI_2 = \exp(i+j*MCH+k*MCHC)/(1+\exp(i+j*MCH+k*MCHC))$$

wherein i, j and k are constants.

7. The method of claim 6, wherein said i, j and k are −97.98, 0.24 and 2.91, respectively.

8. The method of claim 5, wherein said iron deficiency comprises absolute iron deficiency, or functional iron deficiency.

9. A method of producing an iron deficiency index ($IDI_1$) of a blood sample on a hematology analyzer comprising:
 (a) mixing a first aliquot of a blood sample with a blood diluent to form a first sample mixture, analyzing said first sample mixture on said hematology analyzer, and obtaining a mean cell volume of red blood cells (MCV) and a red blood cell concentration (RBC);
 (b) mixing a second aliquot of said blood sample with a reagent system to form a second sample mixture, analyzing said second sample mixture on said hematology analyzer, and obtaining a hemoglobin concentration (Hgb) of said blood sample;
 (c) obtaining mean cell hemoglobin (MCH) using said RBC and said Hgb;
 (d) obtaining said iron deficiency index ($IDI_1$) using said MCV and said MCH, said $IDI_1$ being defined as a logistic regression function of said MCV and said MCH; and
 (e) reporting said $IDI_1$ of said blood sample on said hematology analyzer.

10. The method of claim 9, wherein said $IDI_1$ is defined by following equation:

$$IDI_1 = \exp(a+b*MCV+c*MCH)/(1+\exp(a+b*MCV+c*MCH))$$

wherein a, b and c are constants.

11. The method of claim 10, wherein said a, b and c are −35.6, 0.087 and 1.61, respectively.

12. A method of producing an iron deficiency index ($IDI_2$) of a blood sample on a hematology analyzer comprising:
 (a) mixing a first aliquot of a blood sample with a blood diluent to form a first sample mixture, analyzing said first sample mixture on said hematology analyzer, and obtaining a mean cell volume of red blood cells (MCV) and a red blood cell concentration (RBC);
 (b) mixing a second aliquot of said blood sample with a reagent system to form a second sample mixture, analyzing said second sample mixture on said hematology analyzer, and obtaining a hemoglobin concentration (Hgb) of said blood sample;
 (c) obtaining mean cell hemoglobin (MCH) and mean cell hemoglobin concentration (MCHC) using said MCV, said RBC and said Hgb;
 (d) obtaining said iron deficiency index ($IDI_2$) using said MCH and said MCHC, said $IDI_2$ being defined as a logistic repression function of said MCH and said MCHC; and
 (e) reporting said $IDI_2$ of said blood sample on said hematology analyzer.

13. The method of claim 12, wherein said $IDI_2$ is defined by following equation:

$$IDI_2 = \exp(i+j*MCH+k*MCHC)/(1+\exp(i+j*MCH+k*MCHC))$$

wherein i, j and k are constants.

14. The method of claim 13, wherein said i, j and k are −97.98, 0.24 and 2.91, respectively.

* * * * *